United States Patent [19]

Weisenfeld

[11] Patent Number: 5,286,481
[45] Date of Patent: * Feb. 15, 1994

[54] METHOD OF REDUCING WEIGHT IN MAMMALS

[76] Inventor: Michael S. Weisenfeld, 6018 Wymford Dr., West Bloomfield, Mich. 48322

[*] Notice: The portion of the term of this patent subsequent to Aug. 11, 2009 has been disclaimed.

[21] Appl. No.: 925,091

[22] Filed: Aug. 4, 1992

Related U.S. Application Data

[63] Continuation-in-part of Ser. No. 614,160, Nov. 15, 1990, Pat. No. 5,137,716.

[51] Int. Cl.$^5$ .................... A61K 31/74; A61K 31/14
[52] U.S. Cl. ............................ 424/78.01; 424/78.1; 424/78.16; 514/643; 514/909; 514/911
[58] Field of Search .............. 424/78.10, 78.01, 78.12; 514/909, 911, 78.16, 643

[56] References Cited

U.S. PATENT DOCUMENTS 4,895,723  1/1990  Amer et al. ..................... 424/78.12
5,026,555  6/1991  Killeen ........................... 424/78.12

*Primary Examiner*—Frederick E. Waddell
*Assistant Examiner*—K. Weddington
*Attorney, Agent, or Firm*—Brooks & Kushman

[57] ABSTRACT

Described is a method of decreasing the weight in mammals to a desired level comprising orally administering thereto an effective weight reducing amount of a nontoxic anion exchange resin containing composition for a desired period of time to achieve a desired weight reduction. Compositions useful for reducing weight in patients contain an anion exchange resin such as cholestyramine, colestipol or polidexide, with bran and optionally, artificial sweeteners and flavors.

7 Claims, No Drawings

METHOD OF REDUCING WEIGHT IN MAMMALS

CROSS-REFERENCE TO RELATED APPLICATION

This application is a continuation-in-part of U.S.S.N. 614,160 filed Nov. 15, 1990, now U.S. Pat. No. 5,137,716 entitled "Method of Reducing Weight in Mammals," and incorporated herein by reference.

TECHNICAL FIELD

The invention is concerned with weight reduction in mammals utilizing ion exchange resins.

BACKGROUND ART

Ion exchange resins are used for various therapeutic purposes. U.S. Pat. No. 4,759,923 describes the use of cholestyramine, colestipol and polidexide as bile acid sequestrants and cholesterol lowering agents.

U.S. Pat. No. 4,902,501 teaches the use of a pharmaceutical composition for oral usage endowed with sequestering activity for the biliary acids containing cholestyramine as its active principle further containing at least one anti-microbial agent, one suspending agent and one coating agent.

U.S. Pat. No. 4,797,288 teaches a drug delivery system designed to be chewed or swallowed comprising cholestyramine, a hydrophobic matrix containing an emulsifier and an edible material, a glyceride and a coating material effective to delay hydration until ingested. The coating material forms a protective barrier effective to prevent the unpleasant taste perception for the cholestyramine material.

U.S. Pat. No. 4,790,991 teaches an ingestible aggregate containing a dietary fiber and a drug that is an anti-cholesterol agent such as cholestyramine.

European patent application No. 332,600 teaches a combination of cholestyramine and sorbic acid. European patent application 320,519 teaches the use of corn syrup or sucrose syrup to assist in eliminating the fishy odor of cholestyramine.

U.S. Pat. No. 4,837,255 teaches the use of an improved taste when aspartame is used as a sweetener.

Chewable delivery systems for cholestyramine are taught in U.S. Pat. No. 4,778,676

None of the references teach a method of decreasing weight in mammals by the use of an effective weight reducing amount of an anion exchange resin such as cholestyramine, colestipol or polidexide, particularly when combined with bulking agents and/or artificial sweetening agents and flavors.

SUMMARY OF THE INVENTION

Described is a method of decreasing the weight in mammals to a desired level comprising orally administering thereto an effective weight reducing amount of a non-toxic anion exchange resin for a desired period of time to achieve a desired weight reduction. Compositions useful for reducing weight in patients contain an anion exchange resin such as cholestyramine, colestipol or polidexide, with bran, and optionally, artificial sweeteners and flavors.

DESCRIPTION OF PREFERRED EMBODIMENTS

The need for man to achieve desirable weight levels can be affected by utilizing appropriate weight reduction compositions. It has been found that anion exchange resins are effective as weight reducing agents in mammals. The program for effecting the weight reduction is to utilize a non-toxic anion exchange resin, preferably in conjunction with palatable materials, for a fixed period of time or to achieve the desired weight reduction.

A preferred weight reducing composition contains the anion exchange resin, cholestryamine. The most preferred cholestyramine is Questran brand (trade mark of Mead Johnson for a synthetic anion exchange polymer in which quaternary ammonium groups are attached to a copolymer of styrene and divinyl benzene). The main constituent of Questran is polystyrene trimethyl benzylammonium as $Cl^-$ anion. Particle size ranges from 50–100 U.S. mesh.

A program that has achieved measurable success is to prepare compositions as described below:

4 grams (1½ measured teaspoons) of powdered wheat bran (0 calories);

4 grams of anhydrous cholestyramine (0 calories);

2 grams (2 packets of) Equal brand of Nutrasweet artificial sweetener (4 calories per packet=8 calories);

1 packet of Equal=0.035 gm. (3% of packet by weight) of aspartame plus dextrose and maltodextrin powder as a bulking agent; 0.0965 gm. (96.5% of packet by weight) of powder total added to produce 1 gram/packet including bulking agent powder and aspartame;

0.5 grams 1/9 pkg.) - (2/8 calories) of Kool-aid ® brand (drink mix) powder *without sugar;*

2 cups (520 grams) of cold water and crushed ice mixed; or

½ pkg. of strawberry flavored Alba ® powdered drink mix (35 calories and 10 grams);

2 cups of 2% low-fat milk (approximately 125 calories/cup and 555 grams);

One or the other of the above two drinks is stirred frequently while being ingested and a drink is taken at least two times a day (three doses) if one large meal is eaten (either 2 doses just before the meal or 1 dose just before and 1 dose just after or 2 doses just after the meal) and up to three times a day (maximum of five doses per day) if needed to allay hunger and/or if two large meals per day are taken.

The most preferred composition utilizing cholestyramine is as follows, with (A) denoting Kool-Aid ® brand (unsweetened) and (B) denoting Alba ® brand (powdered strawberry shake mix)+2% lo-fat milk solids:

| Ingredient | Preferred Range (In Grams) | Most Preferred Ranges (% By Weight) |
|---|---|---|
| Cholestyramine | 1 to 4 (0.18% to 0.78%) (0.17% to 0.70%) | (A) 1/545 × 100% to 4/534 × 100% (B) 1/578 × 100% to 4/568 × 100% |
| Sweetening Agent | Effective amount, e.g. 0.07 (0.013%) (0.013%) | (A) 0.07/545 × 100% to (B) 0.07/534 × 100% |
| Fiber | 1 to 8 (0.18% to 1.50%) (0.17% to 1.41%) | (A) 1/545 × 100% to 1/545 × 100% (B) 1/578 × 100% to 8/568 × 100% |
| Bulking Agent | Effective amount, e.g., 1.93 (0.35% to 0.36%) (0.33% to 0.34%) | (A) 1.93/545 × 100% to 1/93/534 × 100% (B) 1.93/578 × 100% to 1.93/568 × 100% |
| Carrier | Effective amount, | (A) 0.2/545 × 100% to |

| Ingredient | Preferred Range (In Grams) | Most Preferred Ranges (% By Weight) |
|---|---|---|
| | e.g. 0.2 to 1.0 (0.04% to 0.19%) 67.0 (12.0% to 12.0%) | 1.0/534 × 100% (B) 67/578 × 100% to 67/568 × 100% |
| Water | 530 (97.24% to 99.25%) 490–497 85.99% to 87.5% | (A) 530/545 × 100% to 530/534 × 100% (B) 497/578 × 100% to 497/568 × 100% |

Total of all ingredients:
(A) = 534 grams to 545 grams
(B) = 568 grams to 578 grams
Carrier + Water (A) = 530 grams to 531 grams
Carrier + Water (B) = 564 grams Another preferred weight reducing composition contains the anion exchange resin, colestipol. Colestipol is a copolymer of diethylenetriamine and oxirane methyl chloride. The most preferred colestipol is Colestid (trademark of The Upjohn Company).

Yet another preferred weight reducing composition contains the anion exchange resin, polidexide (No.7531, The Merck Index, 11th ed, 1989).

While applicant does not wish to be bound by any theory, it is believed that one reason that anion exchange resins are effective as weight reducing agents in mammals, such as humans, is that the patient is satisfied with food sooner. One feels full due to the ingestion of the fluid containing the anion exchange resin, and therefore, one would eat slowly and ingest a smaller quantity of food. Secondly, it is believed that the use of anion exchange resins inhibits fat from foods from being absorbed. Therefore, there is a partial fat malabsorption. In addition, there is a sedative effect, namely that the patient has been found to sleep more soundly due to the utilization of anion exchange resins and this improved sleep reduces hunger as well as total food intake.

Finally, the prevention of bile acid resorption caused by the utilization of anion exchange resins creates a metabolic inefficiency whereby the body utilizes energy to replace some of the cholesterol lost to bile acid binding (failed resorption of bile acids), i.e., the energy required for synthesis of a portion of the cholesterol lost to bile acid binding effect. The calories required to resynthesize a portion of those cholesterol molecules lost to bile acid binding would be like the calories which are used up when one exercises vigorously in calculating calorie balance and expected weight change.

The period of time that one wishes to utilize anion exchange resin containing materials in a weight reduction program is dependent upon the amount of weight reduction that is desired. Generally, the regimen for taking anion exchange resin containing materials is on a daily basis. The length of time would be minimally one week with longer periods of six months to a year depending upon the need for weight reduction.

EXAMPLE 1

Utilizing the program and compositions outlined above, several patients were placed on a cholestyramine regimen as follows.

Patient number one is a male caucasian approximately 50 years in age. The regimen was followed for approximately 6 months where the initial weight was 268 pounds and after the 6 month period, the weight of the individual was 218 pounds.

A second patient was a caucasian female 20 years in age who utilized the regimen outlined above for two weeks. The initial weight was 270 pounds and the final weight was 255 pounds with a weight reduction of approximately 15 pounds.

A third patient was a 13 year old female caucasian. The regimen followed above resulted in a loss of 22 pounds over a three week period of time; the initial weight was 205 pounds and the final weight was 183 pounds.

EXAMPLE 2

For a period of one month, the three patients followed the same regimen detailed above except that the weight reducing composition contained 5 grams of colestipol in place of the cholestyramine. No other changes were made to the composition.

During the one month period, patient number one lost 8 pounds. The second patient lost 10 pounds. Patient number three lost 6 pounds.

While the forms of the invention herein disclosed constitute presently preferred embodiments, mention all of the possible equivalent forms or ramifications of the invention. It is understood that the terms used herein are merely descriptive rather than limiting, and that various changes may be made without departing from the spirit or scope of the invention.

For example, the following drugs may be used in conjunction with the above program, e.g., Chronulac, trademark of G.D. Searle for lactulose, Lorelco, trademark of Dow for probucol, and the like. Additionally, two or more anion exchange resins may be used in combination to achieve the desired weight reduction. Furthermore, in a preferred flavor formulation, various amounts of Perry ® brand orange-flavored, smooth, psyllium mucilloid sweetened with Nutrasweet ® or Equal ® brand of aspartame is substituted for oat bran to enhance palatability. Similarly, the substitution of other high bulk materials to enhance palatability may be made without departing from the spirit or scope of the invention.

What is claimed is:

1. A method of reducing weight in mammals to a desired level comprising orally administering thereto an effective weight reducing amount of an anion exchange resin containing composition for a desired period of time to achieve a desired weight reduction.

2. The method of claim 1 wherein the anion exchange resin containing composition includes a bulking agent.

3. The method of claim 1 wherein the anion exchange resin containing composition includes an artificial sweetening agent.

4. The method of claim 1 wherein the composition containing the anion exchange resin comprises the following materials:

| Ingredient | Weight Range (In Grams) |
|---|---|
| Anion Exchange Resin | 1 to 5 |
| Sweetening Agent | Effective Amount |
| Fiber | 1 to 8 |
| Bulking Agent | Effective Amount |
| Carrier | 0.2 to 6.7 |
| Water | 490–530 |

5. The method of claim 1 wherein the anion exchange resin containing composition is utilized for a minimum of one week.

6. The method of claim 1 wherein the anion exchange resin is colestipol, or a pharmaceutically acceptable salt or mixture thereof.

7. The method of claim 1 wherein the anion exchange resin is polidexide, or a pharmaceutically acceptable salt or mixture thereof.

* * * * *